United States Patent [19]

Lavanish

[11] Patent Number: 4,529,435

[45] Date of Patent: Jul. 16, 1985

[54] HERBICIDALLY ACTIVE ISOXAZOL ACETAL UREAS

[75] Inventor: Jerome M. Lavanish, Akron, Ohio

[73] Assignee: PPG Industries, Inc., Pittsburgh, Pa.

[21] Appl. No.: 369,681

[22] Filed: Apr. 19, 1982

Related U.S. Application Data

[63] Continuation-in-part of Ser. No. 207,151, Nov. 18, 1980, Pat. No. 4,507,145, which is a continuation-in-part of Ser. No. 122,633, Feb. 19, 1980, Pat. No. 4,268,679.

[51] Int. Cl.$^3$ .................... A01N 43/80; C07D 261/14

[52] U.S. Cl. ...................... 71/088; 548/245; 548/246

[58] Field of Search ................. 548/246, 245

[56] References Cited

FOREIGN PATENT DOCUMENTS 0002881 7/1979 European Pat. Off. ............ 548/245
51-63170 6/1976 Japan ..................... 16/342

Primary Examiner—Anton H. Sutto
Attorney, Agent, or Firm—Edward J. Whitfield

[57] ABSTRACT

This invention concerns certain 3-(3- or 5-substituted-5- or -3-yl)-1-substituted-1-(2,2-substituted)ureas having herbicidal activity, and their use to control weeds.

7 Claims, No Drawings

HERBICIDALLY ACTIVE ISOXAZOL ACETAL UREAS

CROSS-REFERENCE TO RELATED APPLICATIONS

This application is a continuation-in-part of copending, commonly assigned application Ser. No. 207,151 filed Nov. 18, 1980, now U.S. Pat. No. 4,507,145 which is a continuation-in-part of application Ser. No. 122,633 filed Feb. 19, 1980, now U.S. Pat. No. 4,268,679.

FIELD OF THE INVENTION

This invention concerns certain acetal ureas, and in particular, 3-(3- or 5-substituted isoxazol-5- or 3-yl)-1-substituted-1-(2,2-substituted)ureas having herbicidal activity, and their use to control weeds.

DESCRIPTION OF THE INVENTION

This invention relates to 3-(3- or 5-substituted-isoxazol-5- or -3-yl)-1-substituted-1-(2,2-substituted)ureas represented by the formula:

$$A-NH-\overset{O}{\underset{\|}{C}}-\overset{R^1}{\underset{|}{N}}-\overset{R^2}{\underset{|}{CH}}-\overset{R^3}{\underset{|}{CH}}-R^6$$

wherein: A is or wherein R is alkyl or haloalkyl of up to 6 carbon atoms; cycloalkyl of from 3 to 8 carbon atoms; alkenyl or alkynyl of up to 5 carbon atoms; $-R^4-O-R^5$ or $-R^4-S-R^5$ wherein $R^4$ is alkylene of up to 6 carbon atoms and $R^5$ is alkyl of up to 6 carbon atoms; or wherein Z is nitro, halogen, trifluoromethyl or $R^5$, and n is 0, 1, 2, or 3;

$R^1$ is alkyl of up to 3 carbon atoms or allyl;

$R^2$ is hydrogen, hydroxy, alkyl of up to 4 carbon atoms, or allyl; and $R^3$ and $R^6$ are the same or different alkoxy or alkylthio of up to 6 carbon atoms or $R^3$ and $R^6$ may join together to form a 5 or 6 membered heterocyclic ring containing up to 3 hetero, i.e., oxygen or sulfur, atoms.

Some alkyl groups of which the various constituents in the above formula are representative are, for example, methyl, ethyl, n-propyl, iso-propyl, n-butyl, iso-butyl, sec-butyl, tert-butyl, pentyl, hexyl, or the like. Exemplary alkoxy and alkythio groups are methoxy, ethoxy, propoxy, butoxy, methoxyethyl, methylthio, ethylthio, butylthio, and the like. As examples of cycloalkyl groups there may be mentioned cyclopropyl, cyclobutyl, cyclopentyl, cyclohexyl, cyclopentyl, and cyclooctyl. Allyl, butenyl, pentenyl, propynyl, butynyl, pentynyl, and the like are exemplary of suitable alkenyl and alkynyl groups represented in the above formula. Representative suitable alkylene groups are, for example, methylene, ethylene, propylene, butylene, pentylene, or hexylene. As the halogen substituents, there may be mentioned chlorine, bromine, iodine, or fluorine, preferably chlorine or bromine.

Although any compound within the scope of the above formula is believed to have herbicidal activity in accordance with this invention, those compounds that have been found to be especially efficacious are 3-(5-t-butylisoxazol-3-yl)-1-methyl-1-(2,2-dimethoxyethyl)urea and 3-(5-t-butylisoxazol-3-yl)-1-methyl-1-(1,3-dioxolan-2-yl methyl)urea.

The compounds of this invention may be conveniently prepared by phosgenating a 5-substituted-3-aminoisoxazole of the formula:

or by reacting a 3-substituted-5-amino isoxazole of the formula:

wherein R is as previously defined with phenyl chloroformate, to prepare the corresponding isocyanate or phenyl carbamate, respectively. The isocyanate or carbamate is then reacted with an equivalent amount of an appropriately substituted amino acetaldehyde acetal of the formula:

$$\overset{R^1}{\underset{|}{NH}}-\overset{R^2}{\underset{|}{CH}}-\overset{R^3}{\underset{|}{CH}}-R^6$$

wherein $R^1$, $R^2$, $R^3$ and $R^6$ are as previously defined, to form a compound of the invention. The preparation of the acetal urea compounds of the invention is more completely described in U.S. Pat. No. 4,268,679, the teachings of which are incorporated by reference herein.

The following Examples are illustrative of the synthesis of certain specific compounds of this invention.

EXAMPLE 1

Preparation of 3-(5-t-butylisoxazol-3-yl)-1-methyl-1-(2,2-dimethoxyethyl)urea:

(a) A 300 milliliter, 3-neck flask equipped with a magnetic stirrer, thermometer, and dry ice condenser/drying tube was charged with 100 milliliters of ethylacetate solution containing 4.8 grams (0.034 mole) of 3-amino-5-(1,1-dimethylethyl)isoxazole. Anhydrous hydrochloric acid gas (10.0 grams) was bubbled into the solution, and then 20 grams of phosgene was bubbled into the solution, which was cooled in an ice bath. The solution was allowed to stand at ambient temperature for 17 hours and then the flask was purged with argon until no $COCl_2$ was detected. The solution was filtered under nitrogen, and the precipitate was washed with benzene to give a precipitate containing about 0.034 mole (5.6 grams) of 5-(t-butyl)isoxazol-3-yl isocyanate.

(b) At ambient temperature, 4.2 grams (0.035 mole) of methylaminoacetaldehyde dimethylacetal in 15 milliliters of benzene was rapidly added to 50 milliliters of benzene solution containing 0.034 mole (5.6 grams) of the precipitate of 5-(t-butyl)isoxazolyl-3-yl isocyanate (prepared above). The resulting slurry was heated to reflux for two minutes, filtered, cooled, and 20 milliliters of hexane added, but no crystals formed upon standing and cooling in a refrigerator. It was then topped on a roto-vac at 70° C. to yield 5.7 grams of a viscous oil containing 3-[5-(t-butyl)-3-isoxazolyl]-1-methyl-1-(2,2-dimethoxyethyl)urea. The oil crystallized on cooling, and the crystals were recrystallized from ethylether/hexane solution with refrigeration. The crystals were removed by suction filtration and air dried to yield 5.2 grams of white crystals of 3-[5-t-butylisoxazol-3-yl]-1-methyl-1-(2,2-dimethoxyethyl)urea. M.P. 80°–84° C., IR spectra (mull.) bands at 3260, 1670, 1600, and 1530 cm$^{-1}$, MS ion at m/e at 285. NMR (CDCl$_3$) 9.11$\delta$ (singlet, 1H); 6.61$\delta$ (singlet, 1H); 4.52$\delta$ (triplet, 1H); 3.42$\delta$ (singlet, 8H); 3.50$\delta$ (doublet, 8H); 3.13$\delta$ (singlet, 3H); 1.30$\delta$ (singlet, 9H).

EXAMPLE 2

Preparation of 3-(5-t-butyl-isoxazol-3-yl)-1-methyl-1-(1,3-dioxolan-2-ylmethyl)urea 14.19 grams (0.085 mole) of 5-t-butyl-isoxazol-3-yl isocyanate prepared as described in paragraph (a) of Example 1, was slurried in a flask with 100 milliliters of toluene. To the slurry was added, dropwise, with stirring, over a 5-minute period at 24° C. (0.085 mole) of N-(1,3-dioxolan-2-ylmethyl)-methylamine in 10 milliliters of toluene. (Note: 19.4 grams of N-(1,3-dioxolane-2-ylmethyl)methylamine was used which due to inert impurities, corresponds to 10 grams of pure material.) The reaction mixture was slowly heated to a temperature of 90° C., at which temperature a clear, pale yellow solution was obtained. Heating was discontinued and the solution was allowed to cool overnight with continuous stirring. The reaction mixture was then cooled in ice bath and the white solid precipitate (presumed to be the inert "impurities" contained in the N-(1,3-dioxalan-2-ylmethyl)-methylamine) was removed by filtration. The mother liquor was concentrated by evaporation giving 15.3 grams of pale yellow oil. Removal of solvent yielded a white crystalline solid, melting at 127.5°–131° C., and identified by IR and NMR spectroscopy as the desired product, 3-[5-(t-butyl)-3-isoxazolyl]-1-methyl-1-(1,3-dioxolan-2-ylmethyl)urea.

The mode of synthesis of specific compounds of this invention have been illustrated by the foregoing Examples; but, it is to be understood that any compound contemplated within the scope of this invention may be prepared by those skilled in the art simply by varying the choice of starting materials and using the illustrated techniques or other suitable techniques.

The compounds of this invention have been found effective in regulating the growth of a variety of undesirable plants, i.e., weeds, when applied in an herbicidally effective amount to the growth medium prior to emergence of the weeds or to the weeds subsequent to emergence from the growth medium. The term "herbicidally effective amount" is that amount of compound or mixture of compounds required to so injure or damage weeds such that the weeds are incapable of recovering following application. The quantity of a particular compound or mixture of compounds applied in order to exhibit a satisfactory herbicidal effect may vary over a wide range and depends on a variety of factors such as, for example, hardiness of a particular weed species, extent of weed infestation, climatic conditions, soil conditions, method of application, and the like. Typically, as little as 0.2 or less pound per acre to 10 or more pounds per acre of compound or mixtures of compounds may be required. Of course, the efficacy of a particular compound against a particular weed species may readily be determined by relatively straightforward laboratory or field testing in a manner well known to the art.

The compounds of this invention may be used as such or in formulation with agronomically acceptable adjuvants, inert carriers, other herbicides, or other commonly used agricultural compounds, for example, pesticides, stabilizers, safeners, fertilizers, and the like. The compounds of this invention, whether or not in formulation with other agronomically acceptable materials, are typically applied in the form of dusts, granules, wettable powders, solutions, suspension, aerosols, emulsions, dispersions or the like, in a manner well known to the art. When formulated with other typically used agronomically acceptable materials, the amount of compound or compounds of this invention present in the formulation may vary over a wide range, for example, from about 0.05 to about 95 percent by weight on weight of formulation. Typically, such formulations will contain from about 5 to about 75 percent by weight of compound or compounds of this invention.

The compounds of this invention as exemplified by the compounds prepared in Examples 1 and 2, have been found effective in controlling a variety of broadleaf and grassy weeds when applied either preemergence or postemergence. The compounds prepared according to Examples 1 and 2 were tested for herbicidal activity against various weed species under controlled laboratory conditions of light, temperature, and humidity, using techniques known to the art. In preemergence evaluation, a solvent solution of the test compound is applied at the desired rate to the weed species prior to emergence from the growth medium whereas in postemergent evaluation, a solvent solution of the test compound is applied at the desired rate directly on the growing plant, the toxic effect of the compound being determined by visual inspection periodically after application.

Each of the compounds prepared in Examples 1 and 2 were individually applied both preemergence and postemergence at an application rate of 10 pounds per acre to common broadleaf and grassy weeds, namely teaweed (*Sida spinosa*), jimson weed (*Datura stramonium*), wild mustard (*Brassica kaber*), yellow nutsedge (*Cyperus esculentus*), yellow foxtail (*Setaria glauca*), large crabgrass (*Digitaria sanguinalis*), johnsongrass (*Sorghum halepense*), coffeeweed (*Daubentonia punicea*), velvetleaf (*Abutilon theophrasti*), tall morningglory (*Ipomoea purpurea Roth*), wild oats (*Avena fatua*), barnyardgrass (*Echinochloa crusgalli*), and cotton, var. DeltaPine 61 (*Gossypium hirsutum*).

Herbicidal efficacies were determined by visual inspection periodically after application and a Numerical Injury Rating assigned, based on a scale of 0 (or injury) to 10 (all plants dead). The following Table gives the Numerical Injury Ratings for the various weed species against which the compounds prepared in Examples 1 and 2 were tested. The Numerical Injury Ratings were determined twenty one (21) days after both preemergence and postemergence applications for the compound of Example 1 and twenty two (22) days after both preemergence and postemergence applications for the compound of Example 2.

TABLE

Preemergence and Postemergence Herbicidal Activities of the Compounds of Examples 1 and 2

| Weed Species | Example 1 Pre | Example 1 Post | Example 2 Pre | Example 2 Post |
|---|---|---|---|---|
| Teaweed | 10 | 10 | 10 | 10 |
| Jimsonweed | 10 | 10 | 10 | 10 |
| Wild mustard | 10 | 10 | 10 | 10 |
| Yellow nutsedge | 5 | 6 | 4 | 1 |
| Yellow foxtail | 10 | 10 | 10 | 6 |
| Large crabgrass | 10 | — | 10 | — |
| Cotton | — | 10 | — | 10 |
| Johnsongrass | 9 | 10 | 10 | 10 |
| Coffeeweed | 10 | 10 | 10 | 10 |
| Tall morningglory | 10 | 10 | 10 | 9 |
| Wild oats | 10 | 10 | 9 | 7 |
| Barnyardgrass | 10 | 10 | 10 | 10 |
| Application Rate, lb/A | 10 | 10 | 10 | 10 |

I claim:
1. A compound represented by the formula:

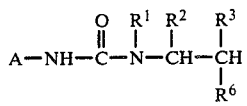

wherein:
A is

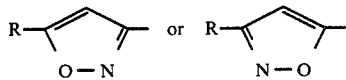

wherein R is alkyl or haloalkyl of up to 6 carbon atoms; cycloalkyl of from 3 to 8 carbon atoms; alkenyl or alkynyl of up to 5 carbon atoms; —R$^4$—O—R$^5$ or —R$^4$—S—R$^5$ wherein R$^4$ is alkylene of up to 6 carbon atoms and R$^5$ is alkyl of up to 6 carbon atoms; or

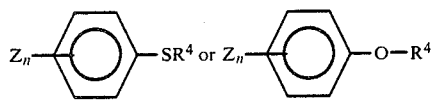

wherein Z is nitro, halogen, trifluoromethyl or R$^5$, and n is 0, 1, 2, or 3;
R$^1$ is alkyl of up to 3 carbon atoms or allyl;
R$^2$ is hydrogen, hydroxy, alkyl of up to 4 carbon atoms, or allyl; and
R$^3$ and R$^6$ are the same or different alkoxy or alkylthio of up to 6 carbon atoms or R$^3$ and R$^6$ may join together to form a 5 or 6 membered heterocyclic ring containing up to 3 hetero, i.e., oxygen or sulfur, atoms.

2. The compound of claim 1 wherein A is

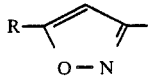

3. The compound of claim 2 wherein R is alkyl.
4. The compound of claim 3 wherein R is tertiary butyl.
5. A compound of claim 4 selected from 3-[5-t-butylisoxazol-3-yl]-1-methyl-1-(2,2-dimethoxyethyl)urea or 3-(5-t-butylisoxazol-3-yl)-1-methyl-1-(1,3-dioxolan-2-ylmethyl)urea.
6. A herbicidal composition containing an agronomically acceptable carrier and a herbicidally effective amount of a compound or mixture of compounds defined in claim 1.
7. In a method of controlling weed growth wherein a herbicidally effective amount of a herbicide is applied to a growth medium prior to emergence of weeds from or applied to the weeds subsequent to emergence from the growth medium, wherein the improvement resides in using as the herbicide a herbicidally effective amount of a compound or mixture of compounds defined in claim 1.

* * * * *